US007556805B2

(12) United States Patent
Houghton et al.

(10) Patent No.: US 7,556,805 B2
(45) Date of Patent: Jul. 7, 2009

(54) COMPOSITIONS FOR TREATMENT OF MELANOMA AND METHOD OF USING SAME

(75) Inventors: Alan N. Houghton, New York, NY (US); Philip J. Bergman, Tarrytown, NY (US); Jedd D. Wolchok, New York, NY (US)

(73) Assignee: Sloan-Kettering Inststute for Cancer Research and The Animal Medical Center, New York, NY (US)

( * ) Notice: Subject to any disclaimer, the term of this patent is extended or adjusted under 35 U.S.C. 154(b) by 1469 days.

(21) Appl. No.: 09/996,128

(22) Filed: Nov. 27, 2001

(65) Prior Publication Data

US 2002/0150589 A1    Oct. 17, 2002

Related U.S. Application Data

(63) Continuation-in-part of application No. 09/627,694, filed on Jul. 28, 2000, and a continuation-in-part of application No. 09/308,697, filed as application No. PCT/US97/22669 on Dec. 10, 1997, now Pat. No. 6,328,969.

(60) Provisional application No. 60/036,419, filed on Feb. 18, 1997, provisional application No. 60/032,535, filed on Dec. 10, 1996, provisional application No. 60/180,651, filed on Jan. 26, 2000.

(51) Int. Cl.
```
A61K 39/00      (2006.01)
A61K 39/38      (2006.01)
A01N 63/00      (2006.01)
A01N 65/00      (2006.01)
A61K 48/00      (2006.01)
C12Q 1/00       (2006.01)
G01N 33/567     (2006.01)
G01N 33/574     (2006.01)
C12P 21/06      (2006.01)
C12N 1/20       (2006.01)
```
(52) U.S. Cl. .................. 424/184.1; 424/93.1; 424/93.2; 424/93.7; 424/277.1; 435/4; 435/7.21; 435/7.23; 435/69.1; 435/252.3; 435/325; 435/348; 435/352; 435/354; 435/366

(58) Field of Classification Search .............. 424/184.1, 424/93.1, 93.2, 93.7, 277.1, 194.1; 435/4, 435/7.21, 7.23, 69.1, 252.3, 325, 348, 352, 435/354, 366
See application file for complete search history.

(56) References Cited

U.S. PATENT DOCUMENTS

| | | | |
|---|---|---|---|
| 5,262,177 A | 11/1993 | Brown et al. | |
| 5,314,813 A | 5/1994 | Peterson et al. | |
| 5,397,703 A | 3/1995 | De Boer et al. | |
| 5,773,291 A | 6/1998 | Bouchard et al. | |
| 6,080,727 A * | 6/2000 | Zupi | ....................... 514/44 |
| 6,328,969 B1 | 12/2001 | Houghton et al. | |

FOREIGN PATENT DOCUMENTS

| | | |
|---|---|---|
| WO | WO 92/17205 | 10/1992 |
| WO | WO 98/04720 | 2/1998 |
| WO | WO 98/25574 | 6/1998 |

OTHER PUBLICATIONS

Disis et al. Peptide-based, but not whole protein, vaccines elicit immunity to HER-2/neu, an oncogenic self-protein. The Journal of Immunology 156: 3151-3158, May 1, 1996.*
Eck et al (Gene Based Therapy in The Pharmacological Basis of Therapeutics, Goodman and Gilman, Eds, 1996, pp. 77-101).*
Zhai et al. Antigen-Specific Tumor Vaccines. The Journal of Immunology 156: 700-710, Jan. 1996.*
Verma and Somia. Gene and therapy-promises, problems and prospects. Nature 389: 239-242, Sep. 1997.*
Miller and Vile. Targeted vectors for gene therapy. FASEB J. 9: 190-199, 1995.*
Deonarain, Mahendra. Ligand-targeted receptor-mediated vectors for gene delivery. Exp. Opin. Ther. Patents 8(1): 53-69, 1998.*
Crystal. Transfer of Genes to Humans: Early Lessons and Obstacles to Success. Science 270: 404-410, Oct. 20, 1995.*
B. Bouchard et al., "Induction of Pigmentation in Mouse Fibroblasts by Expression of Human Tyrosinase cDNA", *J. Exp. Med.*, 1989, vol. 169, pp. 2029-2042.
B. Bouchard et al., "Production and Characterization of Antibodies against Human Tyrosinase", *The Journal of Investigative Dermatology*, 1994, vol. 102, No. 3, pp. 291-295.
J. Rowell et al., "Lysosome-Associated Membrane Protein-1-Mediated Targeting of the HIV-1 Envelope Protein to an Endosomal/Lysosomal Compartment Enhances Its Presentation to MHC Class II-Restricted T Cells", *The American Association of Immunologists*, 1995, pp. 1818-1828.
S. Krishnan et al., "Paving the way towards DNA vaccines", *Nature Medicine*, 1995, vol. 1, No. 6, pp. 521-522.
S. Barclay et al., "Rapid isolation of monoclonal antibodies specific for cell surface differentiation antigens", *Proc. Natl. Acad. Sci. USA*, 1986 vol. 83, pp. 4336-4340.
S. Vijayasaradhi et al., "Intracellular Sorting and Targeting of Melanosomal Membrane Proteins: Identification of Signals for Sorting of the Human Brown Locus Protein, GP75", *The Journal of Cell Biology*, 1995, vol. 130, No. 4, pp. 807-820.

(Continued)

Primary Examiner—Alana M Harris
(74) Attorney, Agent, or Firm—Larson & Anderson, LLC (57) ABSTRACT

Melanoma can be treated in a mammalian subject by administering to the subject an immunologically-effective amount of a xenogeneic melanoma-associated differentiation antigen. For example, genetic immunization with a plasmid containing a sequence encoding human gp75 has been shown to be effective in treatment of dogs with melanoma.

10 Claims, 3 Drawing Sheets

OTHER PUBLICATIONS

D. Pardoll et al., "Exposing the Immunology of Naked DNA Vaccines", *Immunity*, Cell Press, 1995, vol. 3, pp. 165-169.

S. Vijayasaradhi et al., "The Melanoma Antigen gp75 is the Human Homologue of the Mouse b (Brown) Locus Gene Product", *J. Exp. Med.*, 1990, vol. 171, pp. 1375-1380.

G. Adema et al., "Molecular Characterization of the Melanocyte Lineage-specific Antigen gp100", *The Journal of Biology Chemistry*, The American Society for Biochemistry and Molecular Biology, 1994, vol. 269, No. 31, pp. 20126-20133.

A. Houghton et al., "Recognition of Autoantigens by Patients with Melanoma", *Annals New York Academy of Sciences*, 1993, pp. 59-69.

C. Naftzger et al., "Immune response to a differentiation antigen induced by altered antigen: A study of tumor rejection and autoimmunity", *Proc. Natl. Acad. Sci. USA*, 1996, vol. 93, pp. 14809-14814.

F. Ausubel et al., "Expression of Proteins is Insect Cells using Baculoviral Vectors", *Current Protocols in Molecular Biology*, Greene Publishing and Wiley-Interscience, 1990, vol. 8, 16.8.1-16.11-7.

J. Ulmer et al., "Heterologous Protection Against Influenza by Injection of DNA Encoding a Viral Protein", *Science*, 1993, vol. 259, pp. 1745-1749.

C. Tiffs et al., "The Folding and Cell Surface Expression of CD4 Requires Glycosylation", *The Journal of Biological Chemistry*, 1992, vol. 267, No. 5, pp. 3268-3273.

S. Park, "JL1, A Novel Differentiation Antigen of Human Cortical Thymocyte", *J. Exp. Med.*, The Rockefeller University Press, 1993, vol. 178, pp. 1447-1451.

C. Cabañas et al., "Characterization of a CD11c-Reactive Monoclonal Antibody (HCI/I) Obtained by Immunizing with Phorbol Ester Differentiated U937 Cells", *Hybridoma*, 1988, vol. 7, No. 2, pp. 167-177.

N. Nanda et al., "Induction of Anti-Self-Immunity to Cure Cancer", *Cell*, 1995, vol. 82, pp. 13-17.

* cited by examiner

SEQUENCE LISTING

<160> NUMBER OF SEQ ID NOS: 2

<210> SEQ ID NO 1
<211> LENGTH: 6408
<212> TYPE: DNA
<213> ORGANISM: Artificial Sequence
<220> FEATURE:
<221> NAME/KEY: misc_feature
<222> LOCATION: ()..()

-continued

<223> OTHER INFORMATION: vector containing human tyrosinase

<400> SEQUENCE: 1

```
attctgcaga tatccagcac agtggcggcc gctcgagtct agagggcccg tttaaacccg      60
ctgatcagcc tcgactgtgc cttctagttg ccagccatct gttgtttgcc cctcccccgt     120
gccttccttg accctggaag gtgccactcc cactgtcctt tcctaataaa atgaggaaat     180
tgcatcgcat tgtctgagta ggtgtcattc tattctgggg gtgggtgg ggcaggacag       240
caaggggag gattgggaag acaatagcag gcatggtggg gatgcagggg ggggggcg        300
ctgaggtctg cctcgtgaag aaggtgttgc tgactcatac caggcctgaa tcgcccatc      360
atccagccag aaagtgaggg agccacggtt gatgagagct tgttgtagg tggaccagtt      420
ggtgattttg aacttttgct tgccacggga acggtctgcg ttgtcgggaa gatgcgtgat     480
ctgatccttc aactcagcaa agttcgatt tattcaacaa agccgccgtc ccgtcaagtc      540
agcgtaatgc tctgccagtg ttacaaccaa ttaaccaatt ctgattagaa aaactcatcg     600
agcatcaaat gaaactgcaa tttattcata tcaggattat caataccata ttttgaaaa     660
agccgtttct gtaatgaagg agaaaactca ccgaggcagt tccataggat ggcaagatcc     720
tggtatcggt ctgcgattcc gactcgtcca acatcaatac aacctattaa ttttcccctcg    780
tcaaaaataa ggttatcaag tgagaaatca ccatgagtga cgactgaatc cggtgagaat    840
ggcaaaagct tatgcatttc tttccagact tgttcaacag gccagccatt acgctcgtca    900
tcaaaatcac tcgcatcaac caaaccgtta ttcattcgtg attgcgcctg agcgagacga    960
aatacgcgat cgctgttaaa aggacaatta caaacaggaa tcgaatgcaa ccggcgcagg   1020
aacactgcca gcgcatcaac aatattttca cctgaatcag gatattcttc taatacctgg   1080
aatgctgttt tccggggat cgcagtggtg agtaaccatg catcatcagg agtacggata   1140
aaatgcttga tggtcggaag aggcataaat tccgtcagcc agtttagtct gaccatctca    1200
tctgtaacat cattggcaac gctacctttg ccatgtttca gaaacaactc tggcgcatcg    1260
ggcttcccat acaatcgata gattgtcgca cctgattgcc cgacattatc gcgagcccat    1320
ttatacccat ataaatcagc atccatgttg gaatttaatc gcggcctcga gcaagacgtt    1380
tcccgttgaa tatggctcat aacacccctt gtattactgt ttatgtaagc agacagtttt    1440
attgttcatg atgatatatt tttatcttgt gcaatgtaac atcagagatt ttgagacaca    1500
acgtggcttt ccccccccc cctgcagcgt ttcttccttt tccccacccc acccccaag     1560
ttcgggtgaa ggcccagggc tcgcagccaa cgtcggggcg caggccctg ccatagcctc     1620
aggttactca tatatacttt agattgattt aaaacttcat ttttaattta aaaggatcta    1680
ggtgaagatc cttttgata atctcatgac caaaatccct taacgtgagt tttcgttcca    1740
ctgagcgtca gaccccgtag aaaagatcaa aggatcttct tgagatcctt tttttctgcg    1800
cgtaatctgc tgcttgcaaa caaaaaaacc accgctacca gcggtggttt gtttgccgga    1860
tcaagagcta ccaactcttt ttccgaaggt aactggcttc agcagagcgc agataccaaa    1920
tactgttctt ctagtgtagc cgtagttagg ccaccacttc aagaactctg tagcaccgcc    1980
tacatacctc gctctgctaa tcctgttacc agtggctgct gccagtggcg ataagtcgtg    2040
tcttaccggg ttggactcaa gacgatagtt accggataag gcgcagcggt cgggctgaac    2100
ggggggttcg tgcacacagc ccagcttgga gcgaacgacc tacaccgaac tgagatacct    2160
acagcgtgag ctatgagaaa gcgccacgct tcccgaaggg agaaaggcgg acaggtatcc    2220
ggtaagcggc agggtcggaa caggagagcg cacgagggag cttccagggg gaaacgcctg    2280
```

-continued

```
gtatctttat agtcctgtcg ggtttcgcca cctctgactt gagcgtcgat ttttgtgatg    2340
ctcgtcaggg gggcggagcc tatggaaaaa cgccagcaac gcggccttt tacggttcct    2400
ggccttttgc tggccttttg ctcacatgtt ctttcctgcg ttatccctg attctgtgga    2460
taaccgtatt accgccatgc attagttatt aatagtaatc aattacgggg tcattagttc    2520
atagcccata tatggagttc cgcgttacat aacttacggt aaatgcccg cctggctgac    2580
cgcccaacga cccccgccca ttgacgtcaa taatgacgag atctgatata ggtgacagac    2640
gatatgaggc tatatcgccg atagaggcga catcaagctg gcacatggcc aatgcatatc    2700
gatctataca ttgaatcaat attggcaatt agccatatta gtcattggtt atatagcata    2760
aatcaatatt ggctattggc cattgcatac gttgtatcta tatcataata tgtacattta    2820
tattggctca tgtccaatat gaccgccatg ttgacattga ttattgacta gttattaata    2880
gtaatcaatt acggggtcat tagttcatag cccatatatg gagttccgcg ttacataact    2940
tacggtaaat ggcccgcctg gctgaccgcc caacgacccc cgcccattga cgtcaatgat    3000
gacgtatgtt cccatagtaa cgccaatagg gactttccat tgacgtcaat gggtggagta    3060
tttacggtaa actgcccact tggcagtaca tcaagtgtat catatgccaa gtccgccccc    3120
tattgacgtc aatgacggta aatggcccgc ctggcattat gcccagtaca tgaccttacg    3180
ggactttcct acttggcagt acatctacgt attagtcatc gctattacca tggtgatgcg    3240
gttttggcag tacaccaatg ggcgtggata gcggtttgac tcacggggat ttccaagtct    3300
ccaccccatt gacgtcaatg ggagtttgtt ttggcaccaa aatcaacggg actttccaaa    3360
atgtcgtaat aaccccgccc cgttgacgca aatgggcggt aggcgtgtac ggtgggaggt    3420
ctatataagc agagctcgtt tagtgaaccg tcagatcgcc tggagacgcc atccacgctg    3480
ttttgacctc catagaagac accgggaccg atccagcctc cgcggccggg aacggtgcat    3540
tggaacgcgg attcccgtg ccaagagtga cgtaagtacc gcctatagac tctataggca    3600
caccccttg gctcttatgc atgctatact gttttggct tggggcctat acaccccgc    3660
ttccttatgc tataggtgat ggtatagctt agcctatagg tgtgggttat tgaccattat    3720
tgaccactcc cctattggtg acgatacttt ccattactaa tccataacat ggctctttgc    3780
cacaactatc tctattggct atatgccaat actctgtcct tcagagactg acacggactc    3840
tgtatttta caggatgggg tcccattat tatttacaaa ttcacatata caacaacgcc    3900
gtcccccgtg cccgcagttt ttattaaaca tagcgtggga tctccacgcg aatctcgggt    3960
acgtgttccg gacatgggct cttctccggt agcggcggag cttccacatc cgagccctgg    4020
tcccatgcct ccagcggctc atggtcgctc ggcagctcct tgctcctaac agtgaggcc    4080
agacttaggc acagcacaat gcccaccacc accagtgtgc cgcacaaggc cgtggcggta    4140
gggtatgtgt ctgaaaatga gctcggagat tgggctcgca ccgctgacgc agatggaaga    4200
cttaaggcag cggcagaaga agatgcaggc agctgagttg ttgtattctg ataagagtca    4260
gaggtaactc ccgttgcggt gctgttaacg gtggagggca gtgtagtctg agcagtactc    4320
gttgctgccg cgcgcgccac cagacataat agctgacaga ctaacagact gttcctttcc    4380
atgggtcttt tctgcagtca ccgtccacgc gttaatacga ctcactatag ggagacccaa    4440
gctggctagc gtttaaactt aagcttggta ccgagctcgg atccactagt ccagtgtggt    4500
ggaattccgg gaagaatgct cctgctgtt ttgtactgcc tgctgtggag tttccagacc    4560
tccgctggcc atttccctag agcctgtgtc tcctctaaga acctgatgga gaaggaatgc    4620
```

```
tgtccaccgt ggagcgggga caggagtccc tgtggccagc tttcaggcag aggttcctgt    4680
cagaatatcc ttctgtccaa tgcaccactt gggcctcaat ttcccttcac agggqtggat    4740 gaccgggagt cgtggccttc cgtcttttat aataggacct gccagtgctc tggcaacttc    4800
atgggattca actgtggaaa ctgcaagttt ggcttttggg gaccaaactg cacagagaga    4860
cgactcttgg tgagaagaaa catcttcgat ttgagtgccc cagagaagga caaatttttt    4920
gcctacctca ctttagcaaa gcataccatc agctcagact atgtcatccc catagggacc    4980
tatggccaaa tgaaaaatgg atcaacaccc atgtttaacg acatcaatat ttatgacctc    5040
tttgtctgga tgcattatta tgtgtcaatg gatgcactgc ttgggggata tgaaatctgg    5100
agagacattg attttgccca tgaagcacca gcttttctgc cttggcatag actcttcttg    5160
ttgcggtggg aacaagaaat ccagaagctg acaggagatg aaaacttcac tattccatat    5220
tgggactggc gggatgcaga aaagtgtgac atttgcacag atgagtacat gggaggtcag    5280 cacccccacaa atcctaactt actcagccca gcatcattct tctcctcttg gcagattgtc    5340
tgtagccgat tggaggagta caacagccat cagtctttat gcaatggaac gcccgaggga    5400
cctttacggc gtaatcctgg aaaccatgac aaatccagaa ccccaaggct cccctcttca    5460
gctgatgtag aattttgcct gagtttgacc caatatgaat ctggttccat ggataaagct    5520
gccaatttca gctttagaaa tacactggaa ggatttgcta gtccacttac tgggatagcg    5580
gatgcctctc aaagcagcat gcacaatgcc ttgcacatct atatgaatgg aacaatgtcc    5640
caggtacagg gatctgccaa cgatcctatc ttccttcttc accatgcatt tgttgacagt    5700 attttttgagc agtggctccg aaggcaccgt cctcttcaag aagtttatcc agaagccaat    5760
gcacccattg gacataaccg ggaatcctac atggttcctt ttataccact gtacagaaat    5820
ggtgatttct ttatttcatc caaagatctg gctatgact atagctatct acaagattca    5880
gacccagact cttttcaaga ctacattaag tcctatttgg aacaagcgag tcggatctgg    5940
tcatggctcc ttggggcggc gatggtaggg gccgtcctca ctgccctgct ggcagggctt    6000
gtgagcttgc tgtgtcgtca aagagaaag cagcttcctg aagaaaagca gccactcctc    6060
atggagaaag aggattacca cagcttgtat cagagccatt tataaaaggc ttaggcaata    6120
gagtagggcc aaaaagcctg acctcactct aactcaaagt aatgtccagg ttcccagaga    6180
atatctgctg gtatttttct gtaaagacca tttgcaaaat tgtaacctaa tacaaagtgt    6240
agccttcttc caactcaggt agaacacacc tgtctttgtc ttgctgtttt cactcagccc    6300
ttttaacatt ttcccctaag cccatatgtc taaggaaagg atgctatttg gtaatgagga    6360
actgttattt gtatgtgaat taaagtgctc ttattttaaa aaaccgga                 6408
```

<210> SEQ ID NO 2
<211> LENGTH: 6485
<212> TYPE: DNA
<213> ORGANISM: Artificial Sequence
<220> FEATURE:
<221> NAME/KEY: misc_feature
<222> LOCATION: ()..()
<223> OTHER INFORMATION: vector containing murine tyrosinase

<400> SEQUENCE: 2

```
attctgcaga tatccagcac agtggcggcc gctcgagtct agagggcccg tttaaacccg     60
ctgatcagcc tcgactgtgc cttctagttg ccagccatct gttgtttgcc cctcccccgt    120
gccttccttg accctggaag gtgccactcc cactgtcctt tcctaataaa atgaggaaat    180
tgcatcgcat tgtctgagta ggtgtcattc tattctgggg ggtggggtgg ggcaggacag    240
```

-continued

```
caaggggag gattgggaag acaatagcag gcatggtggg gatgcagggg ggggggggcg      300
ctgaggtctg cctcgtgaag aaggtgttgc tgactcatac caggcctgaa tcgccccatc    360
atccagccag aaagtgaggg agccacggtt gatgagagct tgttgtagg tggaccagtt     420 ggtgattttg aactttgct ttgccacgga acggtctgcg ttgtcgggaa gatgcgtgat     480
ctgatccttc aactcagcaa aagttcgatt tattcaacaa agccgccgtc ccgtcaagtc    540
agcgtaatgc tctgccagtg ttacaaccaa ttaaccaatt ctgattagaa aaactcatcg    600
agcatcaaat gaaactgcaa tttattcata tcaggattat caataccata tttttgaaaa    660
agccgtttct gtaatgaagg agaaaactca ccgaggcagt tccataggat ggcaagatcc    720
tggtatcggt ctgcgattcc gactcgtcca acatcaatac aacctattaa tttcccctcg    780
tcaaaaataa ggttatcaag tgagaaatca ccatgagtga cgactgaatc cggtgagaat    840
ggcaaaagct tatgcatttc tttccagact tgttcaacag gccagccatt acgctcgtca    900
tcaaaatcac tcgcatcaac caaaccgtta ttcattcgtg attgcgcctg agcgagacga    960
aatacgcgat cgctgttaaa aggacaatta caaacaggaa tcgaatgcaa ccggcgcagg   1020
aacactgcca gcgcatcaac aatattttca cctgaatcag gatattcttc taatacctgg   1080
aatgctgttt tcccggggat cgcagtggtg agtaaccatg catcatcagg agtacggata   1140
aaatgcttga tggtcggaag aggcataaat tccgtcagcc agtttagtct gaccatctca   1200
tctgtaacat cattggcaac gctacctttg ccatgtttca gaaacaactc tggcgcatcg   1260
ggcttcccat acaatcgata gattgtcgca cctgattgcc cgacattatc gcgagcccat   1320
ttatacccat ataaatcagc atccatgttg gaatttaatc gcggcctcga gcaagacgtt   1380
tcccgttgaa tatggctcat aacacccctt gtattactgt ttatgtaagc agacagtttt   1440
attgttcatg atgatatatt tttatcttgt gcaatgtaac atcagagatt ttgagacaca   1500
acgtggcttt ccccccccc cctgcagcgt ttcttccttt tccccacccc acccccaag    1560 ttcgggtgaa ggcccagggc tcgcagccaa cgtcggggcg gcaggccctg ccatagcctc   1620
aggttactca tatatacttt agattgattt aaaacttcat ttttaattta aaaggatcta   1680
ggtgaagatc cttttgata atctcatgac caaaatccct taacgtgagt tttcgttcca    1740
ctgagcgtca gaccccgtag aaaagatcaa aggatcttct tgagatcctt ttttctgcg    1800 cgtaatctgc tgcttgcaaa caaaaaaacc accgctacca gcggtggttt gtttgccgga   1860
tcaagagcta ccaactcttt ttccgaaggt aactggcttc agcagagcgc agataccaaa   1920
tactgttctt ctagtgtagc cgtagttagg ccaccacttc aagaactctg tagcaccgcc   1980
tacatacctc gctctgctaa tcctgttacc agtggctgct gccagtggcg ataagtcgtg   2040
tcttaccggg ttggactcaa gacgatagtt accggataag gcgcagcggt cgggctgaac   2100
ggggggttcg tgcacacagc ccagcttgga gcgaacgacc tacaccgaac tgagatacct   2160
acagcgtgag ctatgagaaa gcgccacgct tcccgaaggg agaaaggcgg acaggtatcc   2220
ggtaagcggc agggtcggaa caggagagcg cacgagggag cttccagggg gaaacgcctg   2280
gtatctttat agtcctgtcg ggtttcgcca cctctgactt gagcgtcgat ttttgtgatg   2340
ctcgtcaggg gggcggagcc tatggaaaaa cgccagcaac gcggcctttt tacggttcct   2400
ggccttttgc tggccttttg ctcacatgtt ctttcctgcg ttatcccctg attctgtgga   2460
taaccgtatt accgccatgc attagttatt aatagtaatc aattacgggg tcattagttc   2520
atagcccata tatggagttc cgcgttacat aacttacggt aaatggcccg cctggctgac   2580
```

```
cgcccaacga cccccgccca ttgacgtcaa taatgacgag atctgatata ggtgacagac    2640
gatatgaggc tatatcgccg atagaggcga catcaagctg gcacatggcc aatgcatatc    2700
gatctataca ttgaatcaat attggcaatt agccatatta gtcattggtt atatagcata    2760
aatcaatatt ggctattggc cattgcatac gttgtatcta tatcataata tgtacattta    2820
tattggctca tgtccaatat gaccgccatg ttgacattga ttattgacta gttattaata    2880
gtaatcaatt acggggtcat tagttcatag cccatatatg gagttccgcg ttacataact    2940
tacggtaaat ggcccgcctg gctgaccgcc caacgacccc cgcccattga cgtcaatgat    3000
gacgtatgtt cccatagtaa cgccaatagg gactttccat tgacgtcaat gggtggagta    3060
tttacggtaa actgcccact tggcagtaca tcaagtgtat catatgccaa gtccgccccc    3120
tattgacgtc aatgacggta aatggcccgc ctggcattat gcccagtaca tgaccttacg    3180
ggactttcct acttggcagt acatctacgt attagtcatc gctattacca tggtgatgcg    3240
gttttggcag tacaccaatg ggcgtggata gcggtttgac tcacgggat ttccaagtct    3300 ccaccccatt gacgtcaatg ggagtttgtt ttggcaccaa aatcaacggg actttccaaa    3360
atgtcgtaat aaccccgccc cgttgacgca aatgggcggt aggcgtgtac ggtgggaggt    3420
ctatataagc agagctcgtt tagtgaaccg tcagatcgcc tggagacgcc atccacgctg    3480
ttttgacctc catagaagac accgggaccg atccagcctc cgcggccggg aacggtgcat    3540
tggaacgcgg attccccgtg ccaagagtga cgtaagtacc gcctatagac tctataggca    3600 caccccttg ctcttatgc atgctatact gttttttggct tggggcctat acaccccgc     3660 ttccttatgc ataggtgat ggtatagctt agcctatagg tgtgggttat tgaccattat     3720
tgaccactcc cctattggtg acgatacttt ccattactaa tccataacat ggctcttgc    3780 cacaactatc tctattggct atatgccaat actctgtcct tcagagactg acacggactc    3840
tgtattttta caggatgggg tcccatttat tatttacaaa ttcacatata caacaacgcc    3900
gtcccccgtg cccgcagttt ttattaaaca tagcgtggga tctccacgcg aatctcgggt    3960
acgtgttccg gacatgggct cttctccggt agcggcggag cttccacatc cgagccctgg    4020
tcccatgcct ccagcggctc atggtcgctc ggcagctcct tgctcctaac agtggaggcc    4080
agacttaggc acagcacaat gcccaccacc accagtgtgc cgcacaaggc cgtggcggta    4140
gggtatgtgt ctgaaaatga gctcggagat tgggctcgca ccgctgacgc agatggaaga    4200
cttaaggcag cggcagaaga agatgcaggc agctgagttg ttgtattctg ataagagtca    4260
gaggtaactc ccgttgcggt gctgttaacg gtggagggca gtgtagtctg agcagtactc    4320
gttgctgccg cgcgcgccac cagacataat agctgacaga ctaacagact gttcctttcc    4380
atgggtcttt tctgcagtca ccgtccacgc gttaatacga ctcactatag ggagacccaa    4440
gctggctagc gtttaaactt aagcttggta ccgagctcgg atccactagt ccagtgtggt    4500
ggaattctgt gacactcatt aacctattgg tgcagatttt gtatgatcta aaggagaaaa    4560
tgttcttggc tgttttgtat tgccttctgt ggagtttcca gatctctgat ggccattttc    4620
ctcgagcctg tgcctcctct aagaacttgt tggcaaaaga atgctgccca ccatggatgg    4680
gtgatgggag tccctgcggc cagctttcag gcagaggttc ctgccaggat atccttctgt    4740
ccagtgcacc atctggacct cagttcccct tcaaagggt ggatgaccgt gagtcctggc     4800
cctctgtgtt ttataatagg acctgccagt gctcaggcaa cttcatgggt ttcaactgcg    4860
gaaactgtaa gttggatttt gggggcccaa attgtacaga gaagcgagtc ttgattagaa    4920
gaaacatttt tgatttgagt gtctccgaaa agaataagtt cttttcttac ctcactttag    4980
```

-continued

```
caaaacatac tatcagctca gtctatgtca tccccacagg cacctatggc caaatgaaca    5040
atgggtcaac acccatgttt aatgatatca acatctacga cctctttgta tggatgcatt    5100
actatgtgtc aagggacaca ctgcttgggg gctctgaaat atggagggac attgattttg    5160
cccatgaagc accagggttt ctgccttggc acagactttt cttgttattg tgggaacaag    5220
aaattcgaga actaactggg gatgagaact tcactgttcc atactgggat tggagagatg    5280
cagaaaactg tgacatttgc acagatgagt acttgggagg tcgtcaccct gaaaatccta    5340
acttactcag cccagcatcc ttcttctcct cctggcagat catttgtagc agatcagaag    5400
agtataatag ccatcaggtt ttatgcgatg aacacctga gggaccacta ttacgtaatc    5460
ctggaaacca tgacaaagcc aaaaccccca ggctcccatc ttcagcagat gtggaatttt    5520
gtctgagttt gacccagtat gaatctggat caatggatag aactgccaat ttcagcttta    5580
gaaacacact ggaaggattt gccagtccac tcacagggat agcagatcct tctcaaagta    5640
gcatgcacaa tgccttacat atctttatga atggaacaat gtcccaagta cagggatcgg    5700
ccaacgatcc cattttttctt cttcaccatg cttttgtgga cagtattttt gaacaatggc    5760
tgcgaaggca ccgccctctt ttggaagttt acccagaagc caatgcacct atcggccata    5820
acagagactc ttacatggtt cctttctac cgctctatag aaatggtgat ttcttcataa    5880
catccaagga tctgggatat gactacagct acctccaaga gtcagatcca ggcttttaca    5940
gaaattatat tgagccttac ttggaacaag ccagtcgtat ctggccatgg cttcttgggg    6000
cagcactggt gggagctgtt attgctgcag ctctctctgg gcttagcagt aggctatgcc    6060
ttcagaagaa gaagaagaag aagcaacccc aggaggaaag gcagccactc ctcatggaca    6120
aagacgacta ccacagcttg ctgtatcaga gccatctgtg aacatcctag gaaacagagt    6180
gggactgaaa ggttttacct cactcgacct atttgttggt gtttctacaa atttaaacta    6240
gtataaaaca tagaccatag ctgtttggct ttttttcaga cccatgtttt ttcctaagtc    6300
ctagtttcta agaaatgact gggatttgct aaaatatata tatatatata taaataataa    6360
cttactaata gctaaataaa atttcctctt acaactaatt gagctggttt ttatgaatgt    6420
gtcttaatta tttaaacttg aggcacattt ttgttttcct tacttcattg tggatcccaa    6480
gccga                                                                6485
```

COMPOSITIONS FOR TREATMENT OF MELANOMA AND METHOD OF USING SAME

This application is a continuation-in-part of U.S. patent application Ser. No. 09/627,694, filed Jul. 28, 2000, and of U.S. patent application Ser. No. 09/308,697 filed May 21, 1999, now U.S. Pat. No. 6,328,969, which is a § 371 National Phase of International Application No. PCT/US97/22669 filed Dec. 10, 1997. This application claims the benefit under 35 USC § 119(e) of U.S. Provisional Applications Nos. 60/036,419 filed Feb. 18, 1997; 60/032,535 filed Dec. 10, 1996 and 60/180,651 filed Jan. 26, 2000. All of the above-mentioned applications are incorporated herein by reference.

BACKGROUND OF THE INVENTION

This application relates to compositions for treatment of melanoma and to a method of using such compositions. The invention utilizes compositions containing xenogeneic differentiation antigens which are associated with melanoma to provide effective therapy.

Differentiation antigens are tissue-specific antigens that are shared by autologous and some allogeneic tumors of similar derivation, and on normal tissue counterparts at the same stage of differentiation. Differentiation antigens have been shown to be expressed by a variety of tumor types, including melanoma, leukemia, lymphomas, colorectal carcinoma, breast carcinoma, prostate carcinoma, ovarian carcinoma, pancreas carcinomas, and lung cancers. For example, differentiation antigens expressed by melanoma cells include Melan-A/MART-1, Pmel17, tyrosinase, and gp75. Differentiation antigen expressed by lymphomas and leukemia include CD19 and CD20/CD20 B lymphocyte differentiation markers). An example of a differentiation antigen expressed by colorectal carcinoma, breast carcinoma, pancreas carcinoma, prostate carcinoma, ovarian carcinoma, and lung carcinoma is the mucin polypeptide muc-1. A differentiation antigen expressed by breast carcinoma is her2/neu. The her2/neu differentiation antigen is also expressed by ovarian carcinoma. Differentiation antigens expressed by prostate carcinoma include prostate specific antigen, prostatic acid phosphatase, and prostate specific membrane antigen.

Melanocyte differentiation antigens have been shown to be recognized by autoantibodies and T cells of persons with melanoma, and to be relevant autoantigens. Wang et al., *J. Exp. Med.* 183: 799-804 (1996); Vijayasaradhi et al., *J. Exp. Med.* 171: 1375-1380 (1990). Unfortunately, in most cases, the immune system of the individual is tolerant of these antigens, and fails to mount an effective immune response. For the treatment of cancers where the tumor expresses differentiation antigens therefore, it would be desirable to have a method for stimulating an immune response against the differentiation antigen in vivo. It an object of the present invention to provide such a method.

SUMMARY OF THE INVENTION

It has now been found that the tolerance of the immune system for self-derived target differentiation antigens can be overcome and an immune response stimulated by administration of a xenogeneic differentiation antigen (wild-type or mutant) of the same type from a species different from the subject being treated. For example, a mouse differentiation antigen can be used to stimulate an immune response to the corresponding differentiation antigen in a human subject. Administration of altered antigens in accordance with the invention results in an effective immunity against the original antigen expressed by the cancer in the treated subject. Thus, in accordance with a first aspect of the invention, there is provided a method for treating melanoma in a mammalian subject, comprising the step of administering to the subject an immunologically-effective amount of a xenogeneic tmelanoma-associated differentiation antigen.

Therapeutic differentiation antigens based on melanoma differentiation antigens are used in accordance with the invention to treat melanoma in subjects suffering from melanoma. In one embodiment of the invention, a plasmid comprising a sequence encoding a xenogeneic tyrosinase, for example human or murine tyrosinase, under the control of a suitable promoter, is administered to a subject. For example, dogs have been treated using plasmids comprising a DNA sequence encoding human tyrosinase with pronounced clinical benefit.

DETAILED DESCRIPTION OF THE INVENTION

The present invention provides a method for treating melanoma in a subject by stimulating an immune response to a melanoma-associated differentiation antigen. The subject is preferably human, although the invention can be applied in veterinary applications to animal species, preferably mammalian or avian species, as well. For treatments of humans, preferred xenogeneic antigens will be rodent antigens, but could come from other mammals such as dog, cat, cow, or sheep, or from birds, fish, amphibian, reptile, insect or other more distantly related species.

As used in the specification and claims of this application, the term "immune response" encompasses both cellular and humoral immune responses. Preferably, the immune response is sufficient to provide immunoprotection against growth of tumors expressing the target differentiation antigen. The term "stimulate" refers to the initial stimulation of a new immune response or to the enhancement of a pre-existing immune response.

In accordance with the invention, a subject is treated by administering a xenogeneic differentiation antigen of the same type as a target differentiation antigen expressed by melanoma cells of the subject in an amount effective to stimulate an immune response. Thus, for example, if the target differentiation antigen is the gp75 antigen found in melanoma cells and melanocytes, the therapeutic antigen is a xenogeneic gp75 antigen.

Xenogeneic differentiation antigen may be administered as a purified differentiation antigen derived from the source organism. Proteins can be purified for this purpose from cell lysates using column chromatography procedures. Proteins for this purpose may also be purified from recombinant sources, such as bacterial or yeast clones or mammalian or insect cell lines expressing the desired product. Nucleic acid sequences of various differentiation antigens from various non-human sources are known, including mouse tyrosinase (Yamamoto et al., *Japanese J. Genetics* 64: 121-135 (1989)); mouse gp100 (Bailin et al., *J. Invest. Dermatol.* 106: 24-27 (1996)); and rat prostate-specific membrane antigen (Bzdega et al., *J. Neurochem.* 69: 2270-2277 (1997).

Administration of the xenogeneic differentiation antigen can be accomplished by several routes. First, the xenogeneic differentiation antigen may be administered as part of a vaccine composition which may include one or more adjuvants such as alum, QS21, TITERMAX or its derivatives, incomplete or complete Freund's and related adjuvants, and cytokines such as granulocyte-macrophage colony stimulating factor, flt-3 ligand, interleukin-2, interleukin-4 and interleukin-12 for increasing the intensity of the immune response. The vaccine composition may be in the form of a xenogeneic differentiation antigen in a solution or a suspension, or the therapeutic differentiation antigen may be introduced in a lipid carrier such as a liposome. Such compositions will generally be administered by subcutaneous, intradermal or intramuscular route. Vaccine compositions containing expressed xenogeneic differentiation antigen are administered in amounts which are effective to stimulate an immune response to the target differentiation antigen in the subject. The preferred amount to be administered will depend on the species of the subject and on the specific antigen, but can be determined through routine preliminary tests in which increasing doses are given and the extent of antibody formation or T cell response is measured by ELISA or similar tests. T cell responses may also be measured by cellular immune assays, such as cytotoxicity, cytokine release assays and proliferation assays.

Figure 3:
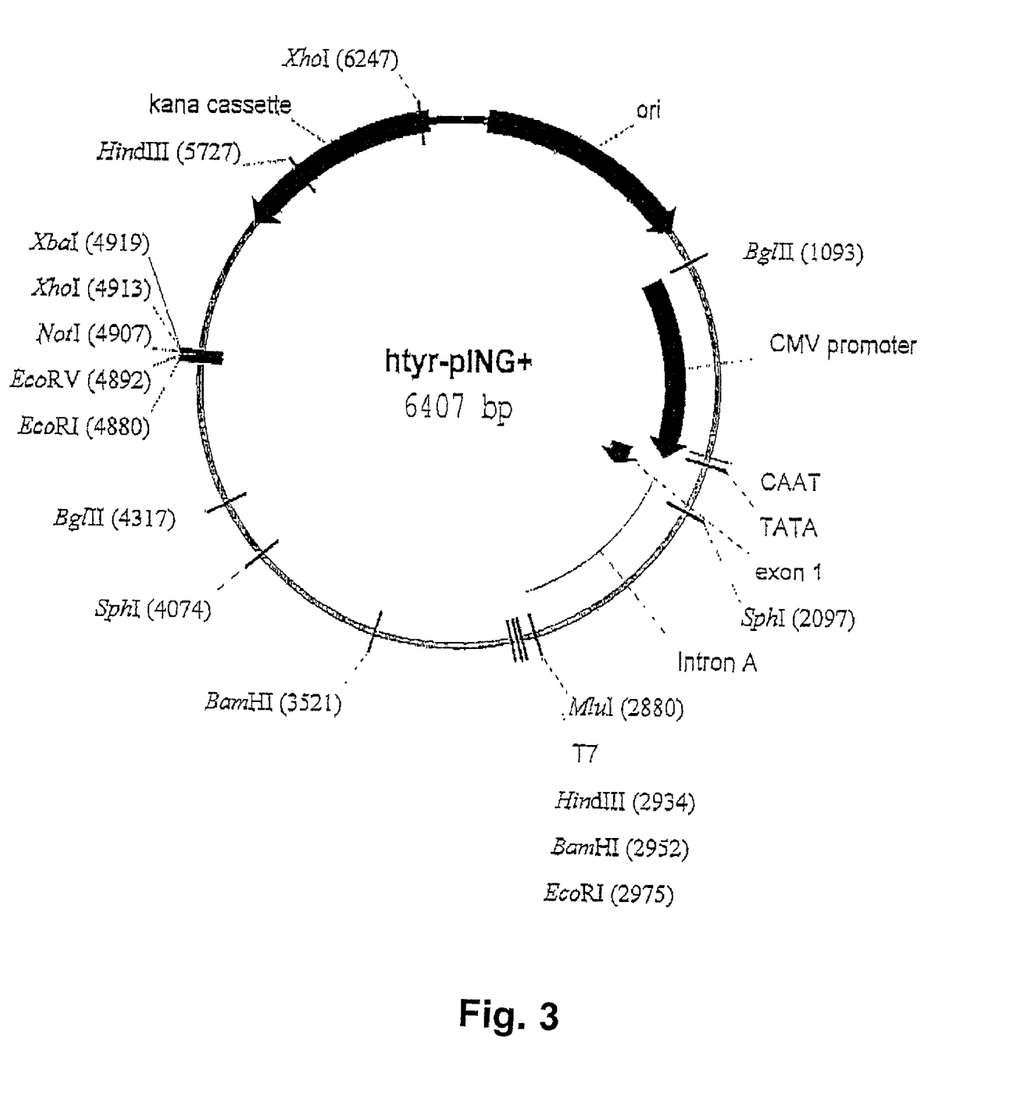
FIG. 3 shows a map and sequence of the vector htyr-pING.
Figure 4:
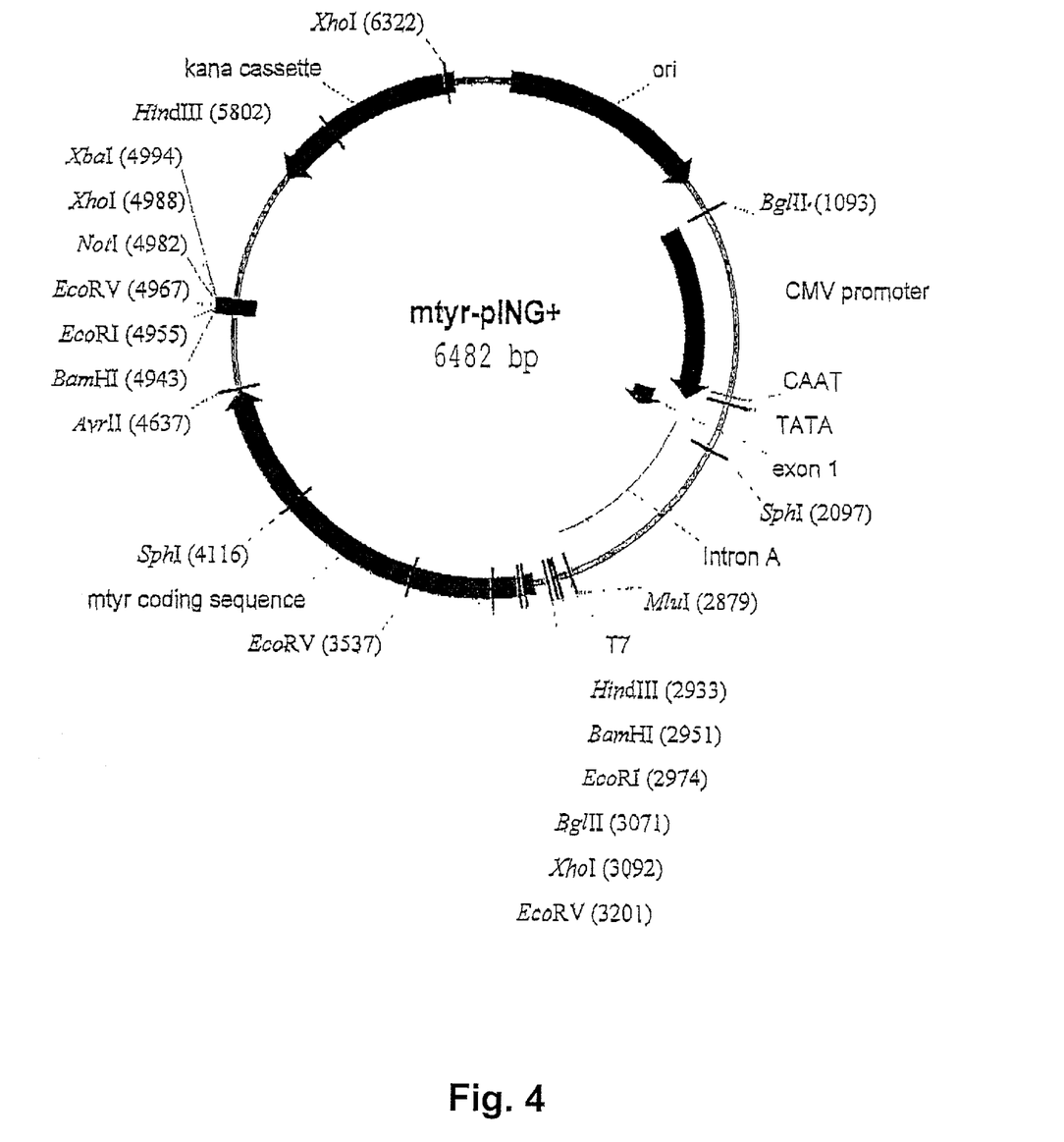
FIG. 4 shows a map and sequence of the vector mtyr-pING.

The xenogeneic differentiation antigen may also be introduced in accordance with the invention using a DNA immunization technique in which DNA encoding the antigen is introduced into the subject such that the xenogeneic differentiation antigen is expressed by the subject. cDNA encoding the differentiation antigen is combined with a promoter which is effective for expression of the nucleic acid polymer in mammalian cells. This can be accomplished by digesting the nucleic acid polymer with a restriction endonuclease and cloning into a plasmid containing a promoter such as the SV40 promoter, the cytomegalovirus (CMV) promoter or the Rous sarcoma virus (RSV) promoter. The resulting construct is then used as a vaccine for genetic immunization. The nucleic acid polymer could also be cloned into plasmid and viral vectors that are known to transduce mammalian cells. These vectors include retroviral vectors, adenovirus vectors, vaccinia virus vectors, pox virus vectors and adenovirus-associated vectors. FIGS. 3 and 4 show restriction maps of two tyrosinase-encoding vectors. The sequences of these vectors are given in Seq. ID. Nos. 1 and 2.

The nucleic acid constructs containing the promoter and the antigen-coding region can be administered directly or they can be packaged in liposomes or coated onto colloidal gold particles prior to administration. Techniques for packaging DNA vaccines into liposomes are known in the art, for example from Murray, ed. "Gene Transfer and Expression Protocols" Humana Pres, Clifton, N.J. (1991). Similarly, techniques for coating naked DNA onto gold particles are taught in Yang, "Gene transfer into mammalian somatic cells in vivo", *Crit. Rev. Biotech.* 12: 335-356 (1992), and techniques for expression of proteins using viral vectors are found in Adolph, K. ed. "Viral Genome Methods" CRC Press, Florida (1996).

For genetic immunization, the vaccine compositions are preferably administered intradermally, subcutaneously or intramuscularly by injection or by gas driven particle bombardment, and are delivered in an amount effective to stimulate an immune response in the host organism. The compositions may also be administered ex vivo to blood or bone marrow-derived cells (which include APCs) using liposomal transfection, particle bombardment or viral infection (including co-cultivation techniques). The treated cells are then reintroduced back into the subject to be immunized. While it will be understood that the amount of material needed will depend on the immunogenicity of each individual construct and cannot be predicted a priori, the process of determining the appropriate dosage for any given construct is straightforward. Specifically, a series of dosages of increasing size, starting at about 0.1 ug is administered and the resulting immune response is observed, for example by measuring antibody titer using an ELISA assay, detecting CTL response using a chromium release assay or detecting TH (helper T cell) response using a cytokine release assay. A clinical trial is being planned in which the vector mtyr-pING (FIG. 4, Seq. ID No. 2) will be administered to human subjects. In this trial, dosages of 100 µg, 500 µg and 1,500 µg will be used. Vaccination will be administered using a BIOJECTOR 2000 jet delivery device every three weeks for a total of six injections.

Once tolerance is broken through the administration of the xenogeneic differentiation antigen, subsequent treatments with syngeneic differentiation may be employed to maintain and in some cases enhance the immune response. (See, Weber, et al., "Tumor immunity and autoimmunity induced by immunization with homologous DNA." *J Clin Invest* 102 (6):1258 (1998).) Thus, in one embodiment of the invention, the subject is first treated by administration of a xenogeneic differentiation antigen (for example for three treatment cycles), and subsequently by administration of a syngeneic differentiation antigen (for example for an additional three treatment cycles). As an alternative to treatment cycles using different therapeutic agents, one can use a single therapeutic agent containing both xenogeneic and syngeneic differentiation antigens. Thus, for example, a mixture of the htyr-pING and mtyp-pING vectors, or a single vector encoding both murine and human tyrosinase under the control of a promoter such that they are expressed in a human subject can be employed for the treatment of melanoma in humans. Vectors are available commercially, for example from Stratagene and other companies, which can express two independent genes. Commonly, these vectors use an internal ribosomal entry site, or IRES, between the two genes. This approach has the advantage of requiring approval for only a single therapeutic agent.

The invention will now be further described with reference to the following, non-limiting examples.

EXAMPLE 1

C57BL/6 mice were immunized with a) syngeneic gp75$^+$ B16 melanoma cells (which express a non-mutant b locus protein); b) syngeneic B16 cells expressing IL-2, GM-CSF and IFN-γ; c) syngeneic gp75$^-$B16 melanoma variant, B78H.1 and syngeneic fibroblasts transfected with cDNA expressing the mouse b allele; d) hydrophilic peptides of gp75 conjugated to carrier protein; and e) full length gp75 glycoprotein purified from syngeneic melanoma cells. Cells, purified glycoprotein or peptides were combined with adjuvants, including Freund's adjuvant, a mixture of bacterial cell wall skeletons and an endotoxin derivative (DETOX), and a saponin component (QS21). Immunizations were tested by intraperitoneal, subcutaneous and intradermal routes. After immunizations, mice were assessed for antibodies against gp75 by ELISA, immunoprecipitation and Western blots, and for cytotoxic T lymphocytes (CTL) to B16 using a $^{51}$Cr-release cell-mediated cytotoxicity assay. As sumunmarized in Table 1, no antibodies or CTL against gp75 were detected after any of these immunization strategies, supporting the conclusion that C57BL/6 maintain tolerance to the gp75 glycoprotein.

EXAMPLE 2

As shown in Example 1, syngeneic C57BL/6 mice immunized with either cell-associated or purified forms of gp75 protein did not produce autoantibodies to gp75. We next assessed whether gp75 encoded by cDNA delivered into the dermis of syngeneic C57BL/6 mice by particle bombardment would induce an autoantibody response.

C57BL/6 mice were genetically immunized with cDNA encoding full-length syngeneic gp75 under the control of a CMV promoter once a week for five weeks. Sera from these mice were then assessed for autoantibodies against gp75 by immunoprecipitation as described in the Materials and Methods. No mouse (0/28) had detectable antibodies, indicating that C57BL/6 mice maintained their tolerance to the syngeneic protein.

EXAMPLE 3

Mice were immunized with the gp75$^+$human melanoma cell line SK-MEL-19 with Freund's adjuvant and evaluated for the development of autoantibodies to murine gp75. All of the mice (20/20) developed autoantibodies. There was no response without adjuvant (0/5 mice), and no antibodies to gp75 were detected in sera of 12 mice immunized with gp75$^-$ human melanomas SK-MEL-131 or SK-MEL-37 plus Freund's adjuvant. Three of five mice immunized with purified human gp75 (10 μg per dose for five immunizations) with Freund's adjuvant developed autoantibodies to gp75, although the antibody responses were generally weaker, possibly due to the lower amount of purified gp75 used compared to the amount of gp75 in SK-MEL-19 lysates. Thus, administration of human gp75 broke the tolerance to gp75 in C57BL/6 mice.

EXAMPLE 4

B16 melanoma cells and normal melanocytes in C57BL/6 mice express GP75, the wild-type b allele of the brown locus. As described above, the product of this locus is recognized by sera from syngeneic mice immunized with mouse gp75 expressed in gp75/Sf9 cells and human gp75. We have previously shown that passive transfer of mouse monoclonal antibody against gp75 into mice bearing B16F10 tumors leads to tumor rejection. Hara et al., *Int. J. Cancer* 61: 253-260 (1995). To determine whether the autoimmune responses observed conferred similar protection against tumors, the in vivo effects of immune recognition of gp75 were investigated using a syngeneic tumor model.

Figure 1:
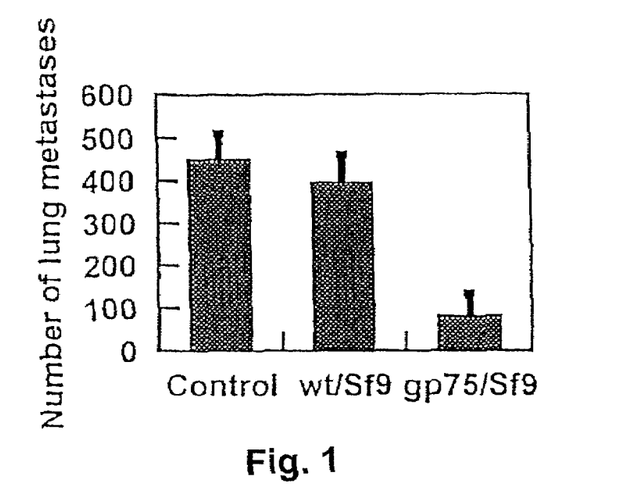
FIG. 1 summarizes the results of a tumor protection experiment using mice immunized with human gp75 expressed in Sf9 insect cells.

Mice (5 mice per group) were injected subcutaneously with gp75/Sf9 lysates (5×10$^6$ gp75/Sf9 cells) concurrently with 10$^5$ B16F10 melanoma cells administered intravenously and the occurrence of lung metastases 14 days after tumor challenge was monitored. Mice immunized with wt/Sf9 cells and unimmunized mice were used as controls. The results are summarized in FIG. 1. As shown, mice immunized with gp75/Sf9 lysates were substantially protected against formation of lung metastases compared to the controls. Significant protection (53% decrease in lung metastases) was also observed when immunization was carried out 4 days after the tumor challenge as metastases become established. There was no significant protection in mice immunized with wt/Sf9 lysates compared to the unimmunized control.

Passive transfer of serum from mice immunized with gp75/Sf9 to five unimmunized mice produced a 68% decrease in lung metastases compared to mice treated with an equivalent amount of normal mouse serum (p=0.02), supporting the conclusion that tumor protection was at least partially mediated by humoral mechanisms.

Mice immunized with human gp75$^+$SK-MEL-19 were also markedly protected against B16F10 melanoma compared to unimmunized mice. (4+/−7 metastases in immunized mice versus 275+/−77 lung metastases in control mice—6 mice per group). Immunization with gp75-melanoma SK-MEL-131 did not introduce tumor protection against B16F10 melanoma, although recognition of other xenogeneic antigens other than gp75 could not be critically assessed.

Mice immunized against the immature, early processed form of gp75, using purified gp75 from gp75/Sf9 cells were not significantly protected against B16F10 metastases (366+/−78 metastases in four immunized mice versus 412+/−94 metastases in five unimmunized control mice). However one mouse in this group did eventually develop autoantibodies against mature gp75 and was protected against lung metastases (only 21 metastases).

EXAMPLE 5

C57BL/6 mice were genetically immunized with cDNA encoding full length human gp75 under control of the control of a CMV promoter once a week for five weeks by gene gun injection. As controls, mice were injected with full length syngeneic mouse gp75 under the control of the CMV promoter, with a glycosylation mutant of gp75 (gly31) or null DNA. Four weeks after the final immunization, the mice were injected through the tail vein with 2×10$^5$ B16F10LM3 melanoma cells. One group of treated mice were also challenged with melanoma cells. Twenty-one days after tumor challenge, mice were sacrificed and surface metastatic lung nodules were scored. There were ten mice in the untreated group, 9 mice in each of the null and mouse gp75 groups, 8 mice in the gly31 group and 19 mice in the human gp75 group. The importance of CD4, CD8 and NK cells was also tested by depletion of using monoclonal antibodies (rat mAb GK1.5 for CD4; mAb 53.6.7 for CD8 and mAb PK1.36 for NK1.1). The necessity of CD4 T cells was also assessed by looking for tumor rejection in CD4 knock-out mice after in vivo transfer of the human gp75 gene by gene gun.

Figure 2:
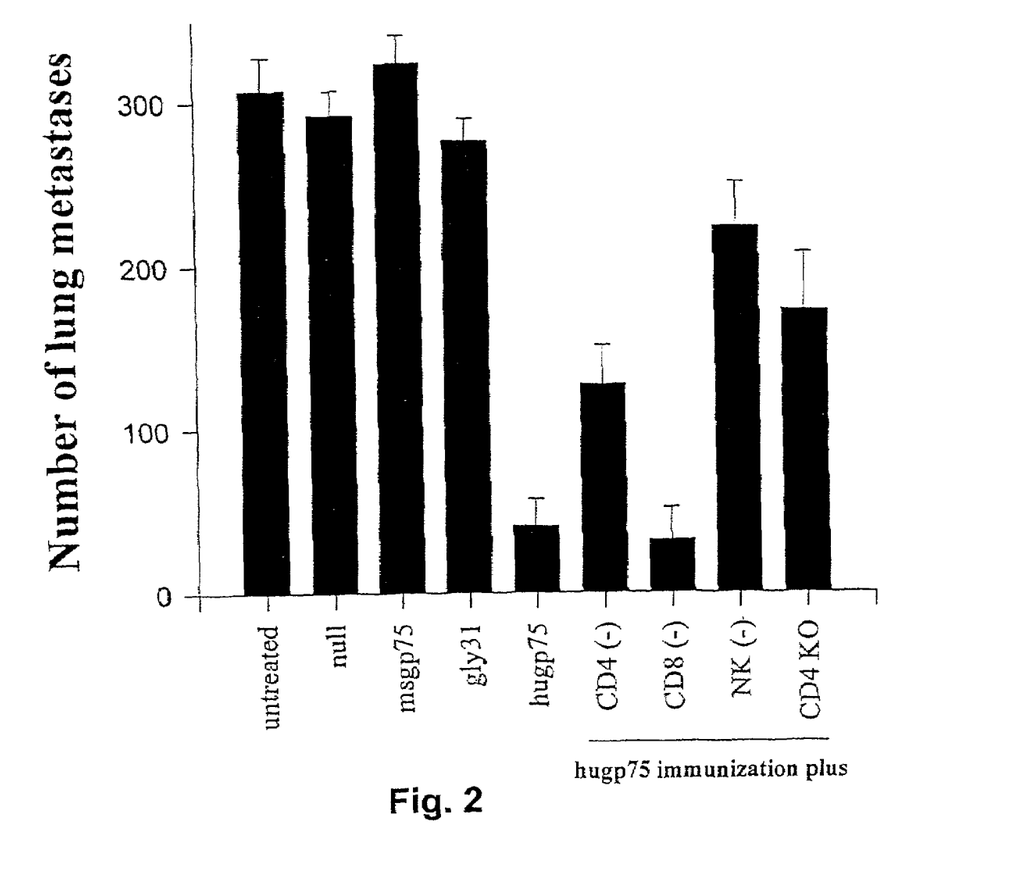
FIG. 2 summarizes the results of a tumor protection using mice immunized by gene gun with DNA encoding xenogeneic human gp75.

As shown in FIG. 2, mice immunized with xenogeneic human gp75 were found to be significantly protected from lung metastases (mean 41±15 metastases) when challenged with B16F10LM3 melanoma (p<0.0001), with an 84% decrease in lung nodules as compared with control mice. Syngeneic mice that received in vivo gene transfer of the glycosylation mutant mouse gp75 were not significantly protected from B16F19 LM3 tumor challenge (mean 300±12 metastases), nor were those that were delivered control DNA (mean 292±15 metastases) by particle bombardment or were left untreated (mean 307±20 metastases) (p>0.45). CD8 deletion did not alter tumor rejection, although depletion of CD4$^+$ (by mAb or knock-out) and NK1.1$^+$cells did result in a reduction in level of protection achieved. Thus these latter cells may play a role in the protection against tumors achieved using genetic immunization with xenogeneic DNA.

EXAMPLE 6

A plasmid containing a sequence encoding human tyrosinase was prepared for genetic immunization and treatment of melanoma in non-human species by introduction of cDNA encoding human tyrosinase into a pING vector. The pING vector contains the following elements: a eukaryotic promoter and enhancer from the CMV virus, a polylinker region to facilitate cloning of a variety of DNA fragments, donor and acceptor splice sites and a polyadenylation signal sequence derived from the bovine growth hormone gene, the ColE1 origin of replication and a gene conferring kanamycin resistance. With the exception of the kanamycin resistance gene, which was cloned as a Pst-I fragment from the plasmid pUC4, all other gene segments were amplified by polymerase chain reaction (PCR). The role of each segment is as follows: the CMV promoter/enhancer and intron A drive the expression of the cDNA chosen as the antigen, and that cDNA is cloned in the polylinker region. The resulting mRNA is processed and polyadenylated using the splice sites and polyadenylation signals. In order to propagate the plasmid in *E. coli*, the colE1 replicon and the kanamycin resistance cassette are included. The kanamycin resistance gene is cloned in the opposite orientation from the tyrosinase cDNA and therefore cannot be transcribed from the CMV promoter in human cells. The CMV promoter/enhancer in pING is fully functional in vivo, as shown by induction of both antibody and cytotoxic T cell responses after DNA immunization of C57BL/6 mice with pING vector expressing tyrosinase, tyrosinase-related protein-2 and ovalbumin genes.

The 2 kb cDNA fragment encoding human tyrosinase has been previously described. Schaed, et al.. "Immunization of Melanoma Patients with both Tyrosinase (370D) and GP100 (210M) Peptides: Comparison of Adjuvants and Peptide Immunogenicity" *Proc Amer Assoc Cancer Res* 41:4029 (2000). An EcoRI fragment containing the tyrosinase cDNA was inserted into the EcoRI site in the polylinker of pING. Orientation was confirmed by bidirectional sequencing. FIG. 3 shows the resulting vector htyr-pING. The sequence of this vector is provided in Seq. ID. No. 1.

EXAMPLE 7

A plasmid containing a sequence encoding murine tyrosinase was prepared for genetic immunization and treatment of melanoma in non-murine species by introduction of cDNA encoding murine tyrosinase into a pING vector. The mouse tyrosinase cDNA was obtained by reverse transcription and PCR amplification of mRNA from B 16 mouse melanoma cDNA. An EcoRI fragment containing the mouse tyrosinase cDNA was inserted into the EcoRI site of the pING polylinker. A map of the resulting vector, mtyr-pING is shown in FIG. 4. The sequence of this vector is given in Seq. ID. No. 2.

EXAMPLE 8

Canine malignant melanoma (CMM) of the oral cavity, nail bed and mucocutaneous junction is a spontaneously occurring, highly aggressive metatstatic neoplasm. CMM is initially treated with aggressive surgery and/or fractionated radiation therapy, however systemic metastatic disease is quite common and invariably chemoresistant. CMM therefore appears to be a good model for advanced human cutaneous melanoma which has similar characteristics.

Three groups of three dogs reach with advanced (WHO Stage II or IV) CMM received four bi-weekly intramuscular injections (100 ug, 500 ug or 1500 ug, respectively per vaccination) of the htyr-pING (example 6) via the Biojector2000 jet delivery device. Pre-vaccination and intermittent post-vaccination blood samples were drawn for routine blood counts, biochemical screening, autoimmune induction and serological/T-cell responses. Minimal to mild pain was noted on vaccination in all nine dogs. No toxicity or induction of autoimmunity was seen in any of the nine dogs. One stage IV dog has had a complete clinical response of lung metastases (durable to 329 days), three dogs have had stable disease (stage III or IV; median followup >6 months) and five dogs have been euthanized due to progression of the primary tumor. All dogs with local tumor progression had little to no local therapy prior to entrance on the study.

The following conclusion can be drawn from this study:
1. Human tyrosinase DNA vaccinations of dogs with advanced malignant melanoma is safe:
   a. No local toxicity at injection site
      i. Physical examination
      ii. Histopathological examination @ necropsy
   b. No systemic toxicity
      i. Hematological
      ii. Biochemical
      iii. ANA assay (anti-dsDNA Ab)
2. Human tyrosinase DNA vaccinations of dogs with advanced malignant melanoma appears to be therapeutic based on:
   a. Prolongation of median survival time (389 days) in comparison to historically reported median survival times (~150-180 days)
   b. Complete response seen in one Stage IV dog for 329 days
   c. No evidence of tumor recurrence nor metastatic disease in 2 dogs (294 & 316 days) that would be expected to not survive>6 months
3. Canine malignant melanoma appears to be a good clinical model for advanced human melanoma as both diseases:
   a. Are spontaneous cancers
   b. Occur in species in similar living environments
   c. Have syngeneic tumors in the respective species
   d. Are locally aggressive
   e. Are widely metastatic to similar metastatic sites
   f. Are chemotherapy & comparatively radiotherapy resistant

The invention claimed is:

1. A method for treating canine malignant melanoma in a dog suffering from canine malignant melanoma comprising administering to the dog an immunologically-effective amount of a xenogeneic differentiation antigen of the same type as a differentiation antigen expressed by melanoma cells of the dog.

2. The method according to claim 1, wherein the xenogeneic melanoma-associated differentiation antigen is tyrosinase.

3. The method according to claim 1, wherein the xenogeneic melanoma-associated differentiation antigen is human tyrosinase.

4. The method according to claim 1, wherein the xenogeneic melanoma-associated differentiation antigen is administered as a vector comprising a DNA sequence encoding the xenogeneic therapeutic melanoma-associated differentiation antigen under the control of a promoter which promotes expression of the xenogeneic melanoma-associated differentiation antigen in the dog.

5. A method for treating canine malignant melanoma in a dog suffering from canine malignant melanoma comprising administering to the dog an immunologically-effective amount of a xenogeneic differentiation antigen of the same type as a differentiation antigen expressed by melanoma cells of the dog, wherein the xenogeneic melanoma-associated differentiation antigen is administered as a vector comprising a DNA sequence encoding the xenogeneic therapeutic melanoma-associated differentiation antigen under the control of a promoter which promotes expression of the xenogeneic melanoma-associated differentiation antigen in the dog, and wherein the vector has the sequence given by Seq. ID. NO. 1.

6. The method according to claim 4, wherein the vector has the sequence given by Seq. ID. NO. 2.

7. A vector comprising the sequence given by Seq. ID No. 1.

8. A vector comprising the sequence given by Seq. ID No. 2.

9. The method of claim 1, wherein the differentiation antigen is selected from the group consisting of Melan-A/Mart-1, Pmel17, tyrosinase and gp75.

10. The method of claim 1, wherein the xenogeneic differentiation antigen is administered by DNA immunization of the subject with DNA encoding the xenogeneic differentiation antigen in a non-viral plasmid vector comprising DNA encoding the xenogeneic differentiation antigen under the control of a promoter which promotes expression of the xenogeneic differentiation antigen.

* * * * *